United States Patent
Ensign et al.

(10) Patent No.: US 7,429,346 B2
(45) Date of Patent: Sep. 30, 2008

(54) METHOD OF FORMING A TEMPORARY PROSTHETIC JOINT USING A DISPOSABLE MOLD

(75) Inventors: Michael D. Ensign, Salt Lake City, UT (US); Matthew M. Lowe, Draper, UT (US); E. Marc Mariani, Salt Lake City, UT (US); Michael H. Bourne, Salt Lake City, UT (US)

(73) Assignee: Ortho Development Corporation, Draper, UT (US)

( * ) Notice: Subject to any disclaimer, the term of this patent is extended or adjusted under 35 U.S.C. 154(b) by 490 days.

(21) Appl. No.: 10/879,683

(22) Filed: Jun. 28, 2004

(65) Prior Publication Data

US 2004/0236429 A1 Nov. 25, 2004

Related U.S. Application Data

(62) Division of application No. 10/389,247, filed on Mar. 13, 2003, now Pat. No. 6,942,475.

(60) Provisional application No. 60/364,061, filed on Mar. 13, 2002.

(51) Int. Cl.
*B29C 33/40* (2006.01)
(52) U.S. Cl. .................... 264/264; 264/313; 623/20.14; 623/20.19; 623/20.21; 623/20.32; 623/901
(58) Field of Classification Search ................. 264/261, 264/313; 623/20.14, 20.19, 20.21, 20.32, 623/901, 2.32
See application file for complete search history.

(56) References Cited

U.S. PATENT DOCUMENTS 4,365,359 A 12/1982 Raab (Continued)

FOREIGN PATENT DOCUMENTS

WO WO 97/26847 * 7/1997

(Continued)

OTHER PUBLICATIONS

Younger et al., Treatment of Infection Associated with Segmental Bone Loss in the Proximal Part of the Femer in Two Stages with Use of an Antibiotic-Loaded Interval Prosthesis, vol. 80-A, No. 1, The Journal of Bone and Joint Surgery, pp. 60-69, Jan. 1998.

(Continued)

*Primary Examiner*—Suzanne E. McDowell
(74) *Attorney, Agent, or Firm*—Matthew D. Thayne; Stoel Rives, LLP (57) ABSTRACT

An orthopedic implant device and method is disclosed. Specifically, a knee mold system is disclosed, including elastic tibial and femoral molds, each of which may be configured and dimensioned as a unitary mold for in situ placement during a surgical procedure. Each mold may be manufactured from an elastic material that may be disposable. The tibial mold may further comprise a sidewall forming a cavity, markings for relative depth measurement, and depth rings for use as a guide for scoring, cutting, and/or trimming and tearing away an excess portion of the tibial mold. The femoral mold may further comprise a sidewall defining a cavity, two legs extending from a body of the femoral mold for forming the artificial condyles, and an eyelet for aiding in placement and removal of the femoral mold. The resulting prosthetic tibial and femoral components may form an articulation surface that mimics, at least in part, the natural articulation surface of the knee.

35 Claims, 4 Drawing Sheets

U.S. PATENT DOCUMENTS

| | | | |
|---|---|---|---|
| 5,123,927 | A | 6/1992 | Duncan et al. |
| 5,226,915 | A | 7/1993 | Bertin |
| 5,641,323 | A | 6/1997 | Caldarise |
| 5,662,158 | A | 9/1997 | Caldarise |
| 5,687,788 | A | 11/1997 | Caldarise et al. |
| 5,788,916 | A | 8/1998 | Caldarise |
| 5,897,592 | A | 4/1999 | Caldarise et al. |
| 6,155,812 | A | 12/2000 | Smith et al. |
| 6,193,761 | B1 | 2/2001 | Treacy |
| 6,296,667 | B1 | 10/2001 | Johnson et al. |

FOREIGN PATENT DOCUMENTS

| | | | |
|---|---|---|---|
| WO | WO 98/20939 | * | 5/1998 |

OTHER PUBLICATIONS

Fehring, et al., Articulating Versus Static Spacers in Revision Total Knee Arthroplasty for Sepsis, No. 380, Clinical Orthopaedics and Related Research, pp. 9-16, Nov. 2000.

Hoffman et al., Treatment of Infected Total Knee Arthroplasty Using an Articulating Spacer, No. 321, Clinical Orthopaedics and Related Research, pp. 45-54, Dec. 1995.

Haddad et al., The PROSTALAC functional spacer in two-stage revision for infected knee replacements, vol. 82-B, No. 6, The Journal of Bone and Joint Surgery, pp. 810-812, Aug. 2000.

Goldstein et al., Temporary Articulating Methylmethacrylate Antibiotic Spacer (TAMMAS), vol. 83, The Journal of Bone and Joint Surgery, pp. 92-97, 2001.

* cited by examiner

METHOD OF FORMING A TEMPORARY PROSTHETIC JOINT USING A DISPOSABLE MOLD

CROSS-REFERENCE TO RELATED APPLICATIONS

This application is a divisional of U.S. patent application Ser. No. 10/389,247, filed Mar. 13, 2003, now U.S. Pat. No. 6,942,475 entitled "DISPOSABLE KNEE MOLD," which claims the benefit of U.S. Provisional Application No. 60/364,061, filed Mar. 13, 2002, which applications are hereby incorporated by reference herein in their entireties, including but not limited to those portions that specifically appear hereinafter, the incorporation by reference being made with the following exception: In the event that any portion of the above-referenced applications is inconsistent with this application, this application supercedes said portion of said above-referenced applications.

STATEMENT REGARDING FEDERALLY SPONSORED RESEARCH OR DEVELOPMENT

Not Applicable.

BACKGROUND OF THE INVENTION

1. The Field of the Invention

The present invention relates generally to implants for use in orthopedic surgery, and more particularly, but not necessarily entirely, to molds for forming temporary orthopedic implants in the knee.

2. Description of Related Art

The anatomy of the knee is primarily composed of two major bones, the tibia and the femur. These two bones meet to form a hinge joint between the proximal tibia and the distal femur. The knee joint is protected by the patella, or the kneecap. The knee joint is cushioned by articular cartilage that covers the ends of the tibia and femur, as well as the underside of the patella. The lateral meniscus and medial meniscus are pads of cartilage that further cushion the joint, acting as shock absorbers between the bones.

A healthy knee joint is able to withstand great forces that are exerted as the knee flexes and extends and supports the weight of the body. However, when the knee joint becomes diseased, damaged or is otherwise unable to withstand the forces required of that joint, it may become necessary to reconstruct or replace the knee joint. When replacement is necessary, the natural knee joint is replaced with a prosthetic knee joint. A typical prosthesis includes a femoral component and a tibial component. During a replacement knee surgery, typically portions of both the tibia and femur must be resected to allow the placement of prosthetic tibial and femoral components, which are anchored to the respective bones.

Sometimes, a small percentage of patients who undergo a total knee replacement surgery suffer from infections in the knee joint at the surgical site. To alleviate the effects of the infection, a two-stage revision of the failed knee replacement is necessary. The two-stage revision includes the following procedures. First, the prosthesis must be surgically removed and the site debrided and cleansed extensively in order to rid the site of the infection. Before a new, permanent prosthesis can be placed in the old surgical site, the site must be free of infection. It is typical for a temporary antibiotic-impregnated cement spacer to be used as part of the therapy to rid the site of infection. Disinfecting the site of infection may take between 6-8 weeks and 3-4 months in most circumstances. Therefore, it is common for surgeons to replace the old prosthetic knee with a temporary implant, typically made of bone cement, during the 6-8 week period while the infection is cleared up and before the new prosthesis is surgically implanted. The second and final step requires a separate revision surgery to then replace the temporary implant with a permanent prosthetic implant.

In the past, surgeons have been left to their own devices when forming cement implants, including the use of negative molds. The process of making a negative mold consists of the surgeon creating a mold by inserting a portion of bone cement into a bowl or other mixing container and allowing the cement to nearly cure. Prior to complete curing of the bone cement, the surgeon inserts the articulating end of the femoral component into the bone cement to create a mold. Using that mold, the surgeon then applies an oil to the mold creating a barrier for separating the cement implant from the cement mold. After applying the oil, cement may be poured into the mold allowing it cure, after which the surgeon attaches the resulting bone cement implant onto the femur as a temporary replacement. Negative molds may be used for both femoral and tibial components alike.

Other methods used in the past of forming temporary implants include surgeons creating the implant with their own hands or simply putting a block of cement between the tibia and the femur to act as a spacer. However, there are many problems associated with such methods and designs, namely increased surgical time due to the preparation and formation time needed for creating the implant. Particular problems associated with the block or spacer method include completely immobilizing the knee in an extended position, after surgery, for the entire 6-8 week period, which in turn leads to soft tissue damage and further complicates the revision surgery. Therefore, reproducing the knee joint using temporary implants that simulate the natural tibial and femoral components of the knee joint is much more desirable because it permits the patient to move his/her leg through a minimal range of motion. The range of motion, while limited, significantly increases the patient's comfort over the 6-8 week period allowing the patient to bend his/her knee for sitting in a chair or for riding in a car and also increases the ease of the revision surgery because the soft tissue has not been damaged to the same extent as when the knee is completely immobilized.

Attempts have been made in the prior art to provide alternatives to surgeons creating their own negative molds or even molding a temporary implant by hand. For example, U.S. Pat. No. 6,155,812 (granted Dec. 5, 2000 to Smith et al.) discloses a cement mold for use in forming a temporary orthopedic implant used in an orthopedic surgical procedure, said mold including a first and second mold joined together by a coupling mechanism. This device is characterized by several disadvantages, including the need for many different sized molds to accommodate the differences in size of patients tibias and femurs, the need for multiple pieces that must be joined together and the need to use the mold outside the patient's knee joint such that the implant must first be formed and then attached to the tibia or femur in two separate steps.

There are several other temporary bone cement molds known in the prior art, such as that disclosed in an article entitled "Temporary Articulating Methylmethacrylate Antibiotic Spacer (TAMMAS)—A New Method of Intraoperative Manufacturing of a Custom-Articulating Spacer" found in *The Journal of Bone and Joint Surgery* 83:S92-97 (2001). This reference discloses a method of conforming sterilized, heavy aluminum foil to the distal portion of the femur or the proximal portion of the tibia such that an aluminum mold is created. Bone cement is later poured into the mold and the cement is formed into the shape of the femoral or tibial component. However, this technique is disadvantageous because it requires the surgeon to conform the foil to the bone and to further form the bone cement into the shape of a femoral or tibial component. In this setting, another disadvantage in the aluminum foil is its ductility. The foil is unable to spring back into its original shape or position making it very difficult to work with and to maintain its shape as the cement is poured into the mold and while the cement is allowed to cure.

Other attempts have been made to provide a mold that is capable of maintaining its original shape. However, such attempts have proven to be unsuccessful because the rigid, non-resilient nature of the materials used, such as metal or a metal alloy. The rigid, non-resilient nature of a metal mold allows the mold to be used repeatedly. However, there are several disadvantages associated with non-resilient molds, for example, non-resilient molds do not have the requisite flexibility to be used in situ, as it is difficult to remove the implant from the mold and there is no flexibility for the mold to be conformed to various anatomical differences in the bones.

It is noteworthy that none of the prior art, known to applicants, provides an elastic mold capable of being attached in situ that further provides for a one piece mold capable of attaching to various sized bone components. There is a long felt need, illustrated by the statistics of increased surgical success of the revision surgery when a patient has a limited range of motion in the knee joint, for an elastic mold for in situ surgical use that allows the bone cement replacement implant to conform to the shape of the knee bones.

The prior art is thus characterized by several disadvantages that are addressed by the present invention. The present invention minimizes, and in some aspects eliminates, the above-mentioned failures, and other problems, by utilizing the methods and structural features described herein.

The features and advantages of the invention will be set forth in the description which follows, and in part will be apparent from the description, or may be learned by the practice of the invention without undue experimentation. The features and advantages of the invention may be realized and obtained by means of the instruments and combinations particularly pointed out in the appended claims.

BRIEF DESCRIPTION OF THE DRAWINGS

The above and other features and advantages of the invention will become apparent from a consideration of the subsequent detailed description presented in connection with the accompanying drawings in which.

DETAILED DESCRIPTION OF THE INVENTION

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would normally occur to one skilled in the relevant art and having possession of this disclosure, are to be considered within the scope of the invention claimed.

Before the present device and methods for surgically positioning the disposable knee mold, in situ, are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It will be appreciated that while the present invention will be described in connection with a knee and as a mold system for a knee, the principles of the present invention may be applied equally to other areas of the body and in other joints, for example, the hip joint or the shoulder joint.

Applicants have discovered that the surgical attachment of knee implants is greatly enhanced by using an elastic mold, in situ, to cast the tibial and femoral components of the knee implant, complete with articulating surfaces that simulate the biomechanics of the natural bone, by utilizing bone cement or other compounds known in the art for creating articulating surfaces, thus simulating the articulating surfaces of the natural knee joint. Applicants have thus conceived of an elastic mold system capable of in situ attachment of an implant onto the bones of the knee joint that may be utilized on several different sizes of bones and that may be easily removed or separated from the resulting implant and bone after the implant has been formed.

The elastic tibial mold and elastic femoral mold of the present invention together form a temporary prosthetic implant that may be used as a temporary knee replacement when a patient's knee joint requires a total knee replacement surgery or a revision knee replacement surgery, when the knee contains an infection. Prior to implanting a permanent knee replacement, the infection in the knee must be eliminated through debridement and loading the infected area with antibiotics. Loading the infected area with an antibiotic directly, and also loading the biocompatible material used to form the temporary prosthetic implant with antibiotics, and thereafter implanting said temporary prosthetic implant into the bone, is considered to be an effective process for eliminating the infection. After 3-4 months, the infected area should be ready to receive a permanent prosthetic knee implant. Applicants have discovered a way to accomplish the above process by utilizing the tibial mold and femoral mold of the present invention to form said temporary prosthetic implant directly on the bone, in situ, during surgery. The elastic tibial mold and femoral mold aid in the process of distributing antibiotic to the infected area of the bone, while permitting some range of motion in the knee joint while the infected area is healing.

Figure 1:
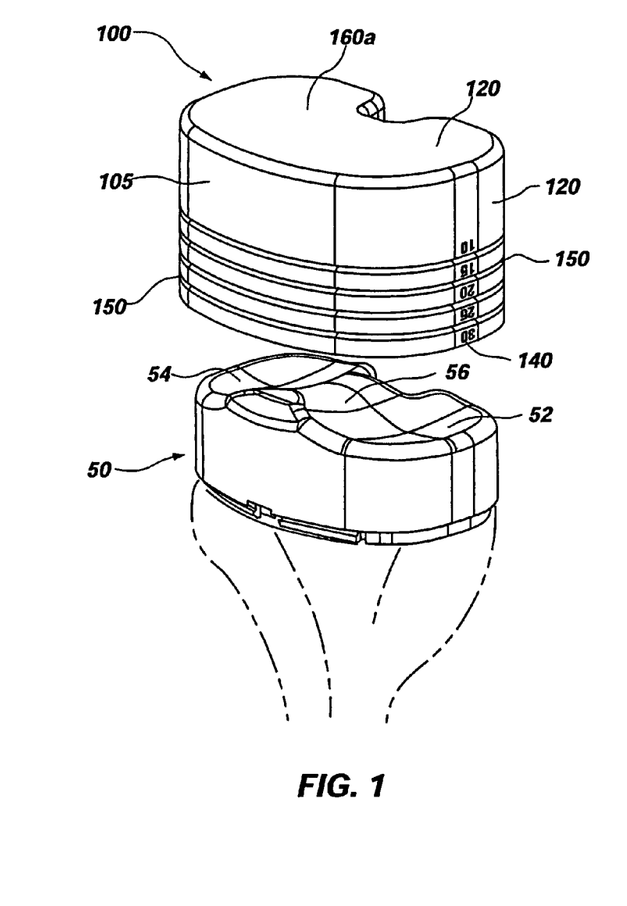
FIG. 1 is a perspective view of a tibial mold and resulting tibial implant made in accordance with the principles of the present invention.
Figure 2:
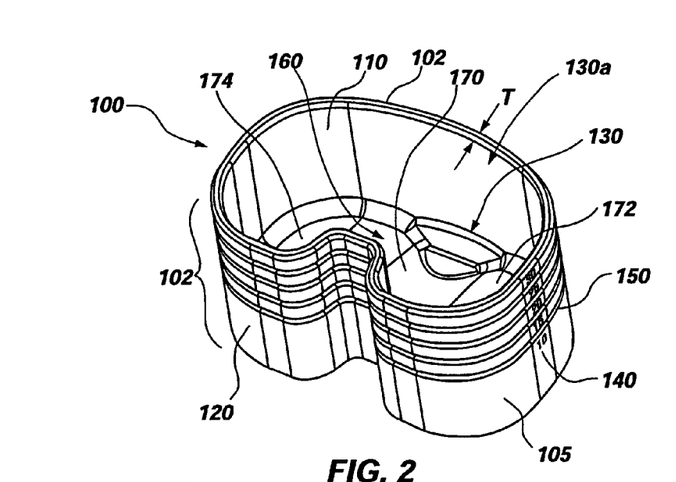
FIG. 2 is a perspective view of the tibial mold of FIG. 1, with the top of the mold turned upside down illustrating an interior cavity.
Figure 3:
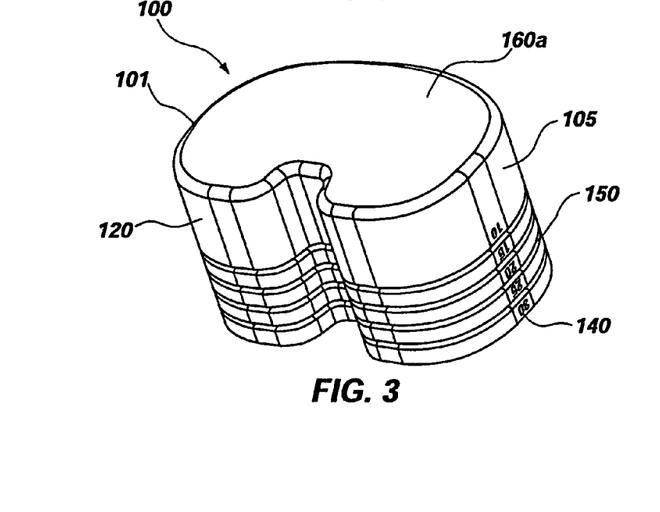
FIG. 3 is a perspective view of the tibial mold of FIG. 1, with the mold illustrated in an upright position.
Figure 4:
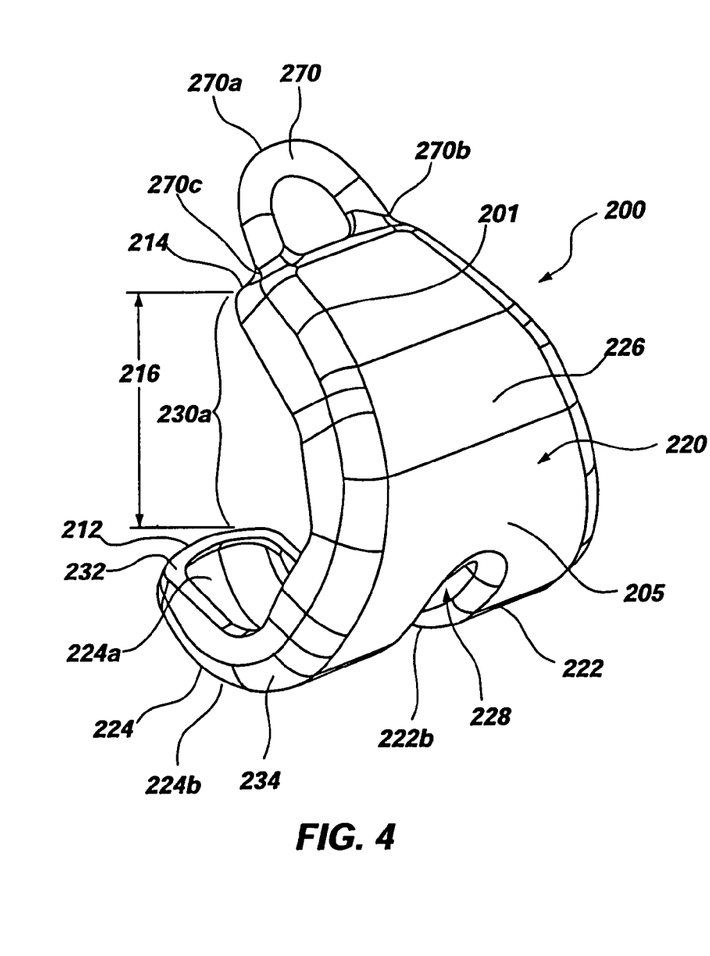
FIG. 4 is a perspective, rear view of a femoral mold made in accordance with the principles of the present invention.
Figure 5:
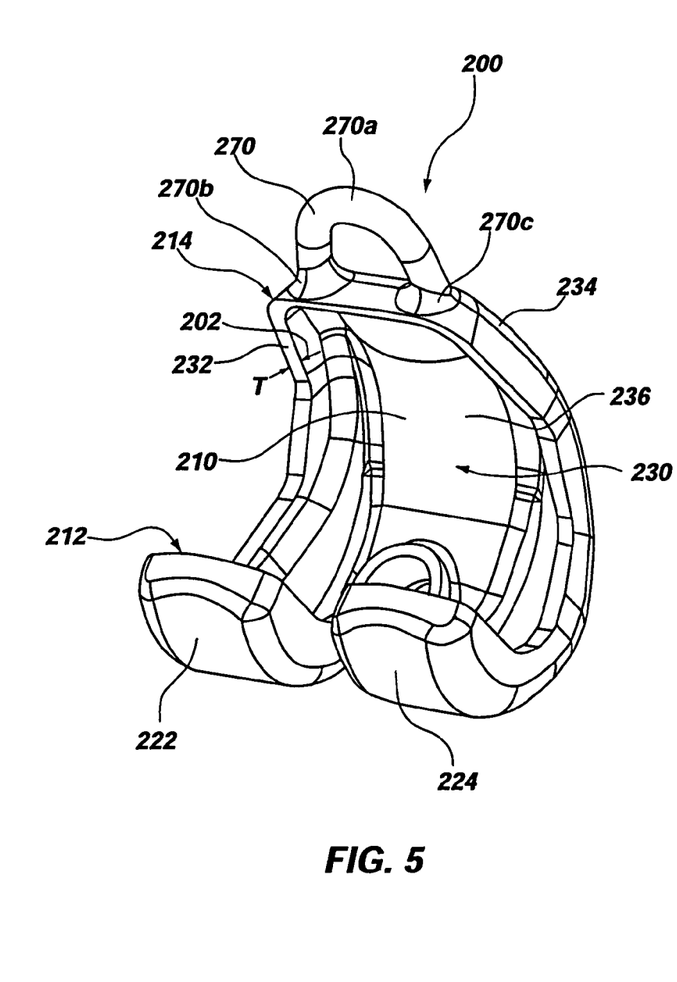
FIG. 5 is a perspective, front view of the femoral mold of FIG. 4 illustrating an interior cavity.
Figure 6:
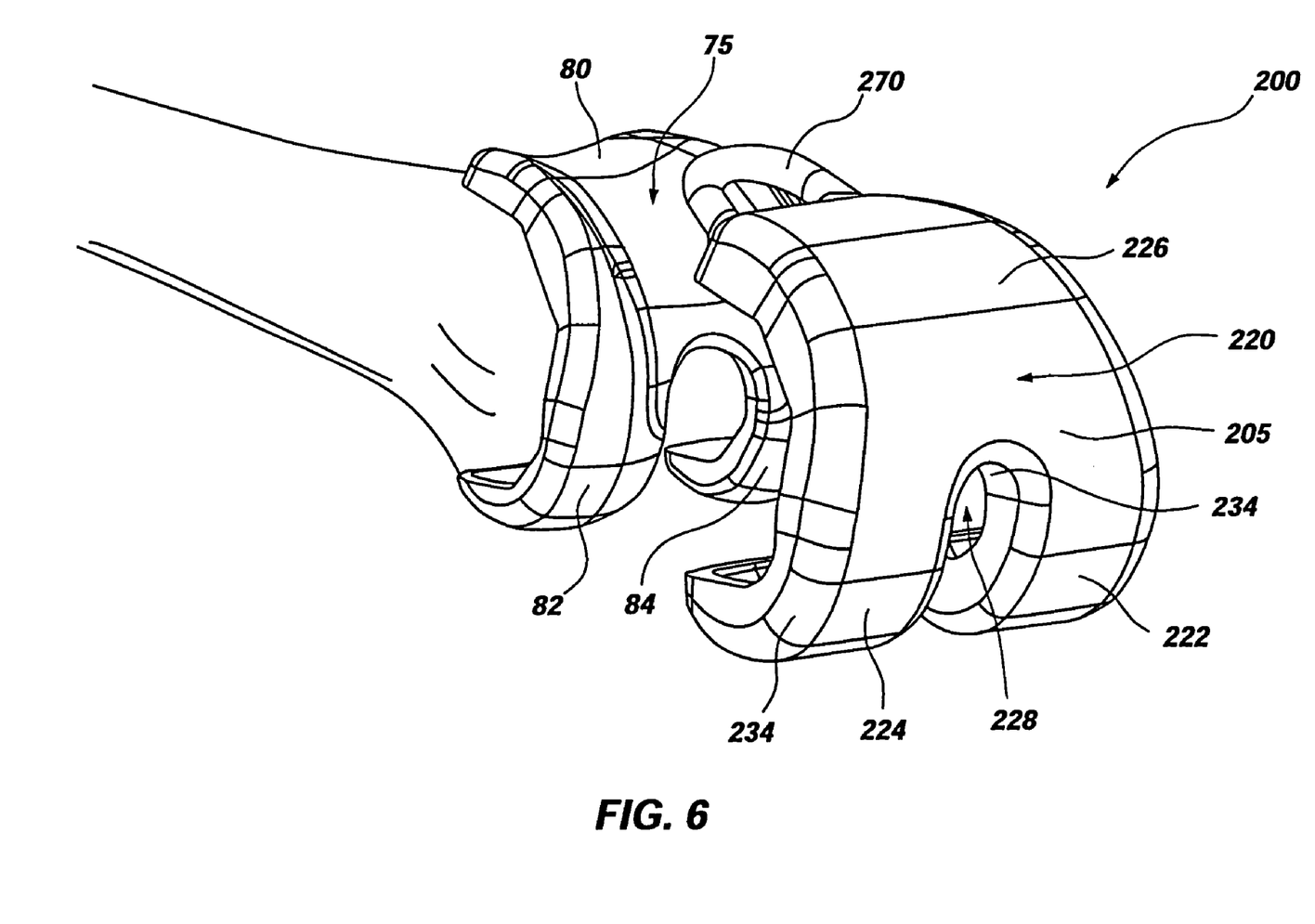
FIG. 6 is a perspective view of a femoral mold and the resulting femoral implant made in accordance with the principles of the present invention.
Figure 7:
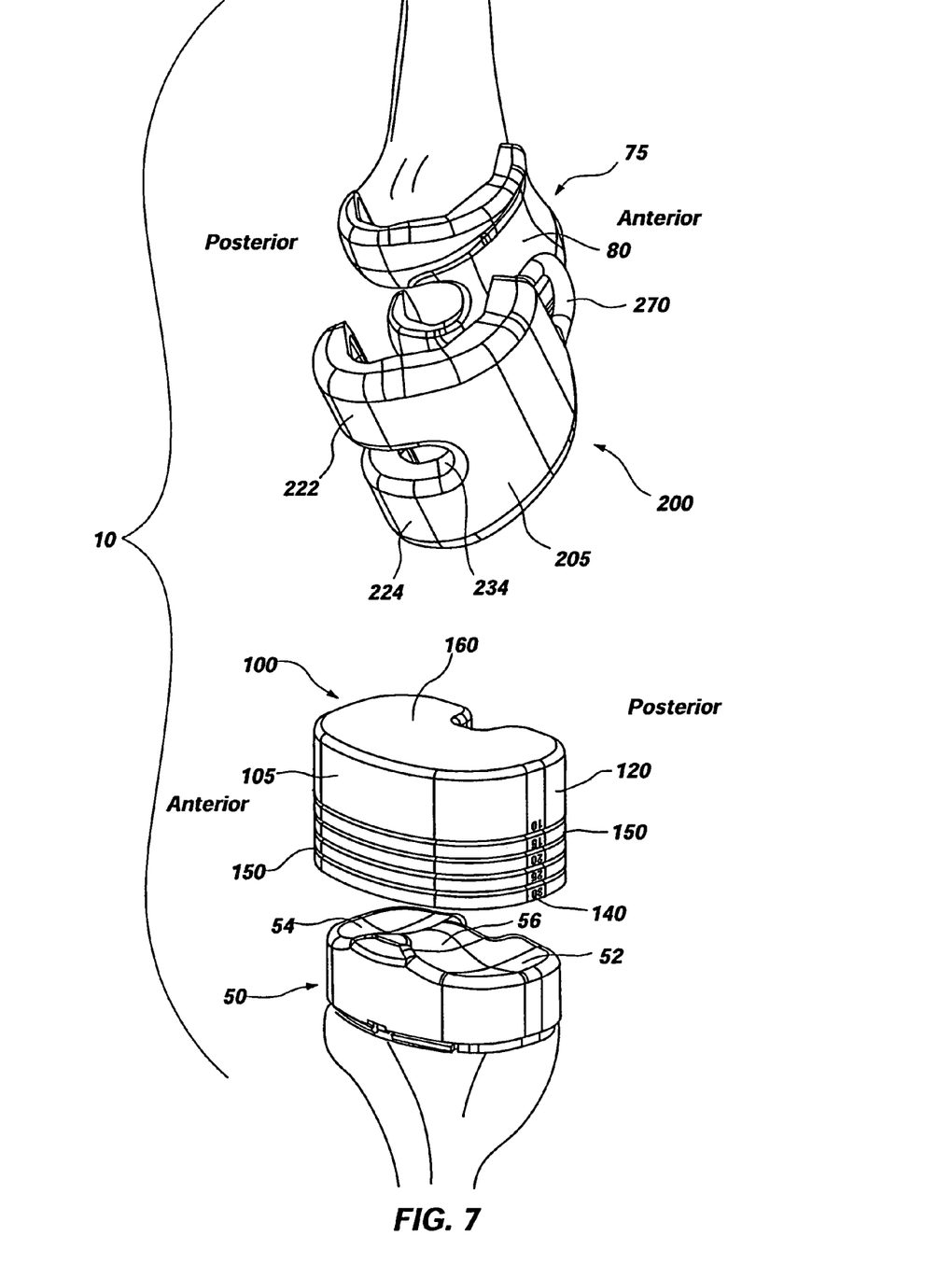
FIG. 7 is a perspective view of the femoral mold with the resulting femoral implant and the tibial mold with the resulting tibial implant together comprising a mold system made in accordance with the principles of the present invention.

Referring now to the figures, a disposable knee mold system 10 (illustrated best in FIG. 7) is illustrated for creating a knee replacement in accordance with the present invention, which may generally comprise two components, a tibial mold 100, illustrated in FIGS. 1-3, and a femoral mold 200, illustrated in FIGS. 4-6. It will be appreciated that both the tibial mold 100 and the femoral mold 200 may be manufactured from an elastic material, such as silicone or a rubber material, or any other polymeric material that exhibits similar physical properties as silicone, namely elasticity and biocompatibility. It will be appreciated that the material used to manufacture the tibial mold 100 and the femoral mold 200 must not adversely react with the biocompatible material used to form the prosthetic implants 50 and 75. It should be noted that the tibial mold 100 and the femoral mold 200 may also be made of any other material which exhibits similar elastic properties as silicone. It will be appreciated that the tibial mold 100 and the femoral mold 200 may both be manufactured from said elastic material and may be designed for one time use and then disposed of, thus creating a mold system that may be scored, cut, trimmed or otherwise altered by a surgeon at the time of surgery in order to accommodate the differing anatomies of each patient.

It will be appreciated that the femoral mold 200 forms a femoral component 75, or a first portion, of the entire prosthetic implant, while the tibial mold 100 forms a tibial component 50, or a second portion, of the prosthetic implant. It should be noted that any suitable elastic material currently known, or which may become known in the future, in the art for manufacturing an elastic mold system and which accomplishes the principles and designs of the present invention as disclosed herein is intended to fall within the scope of the present invention.

Further, the tibial mold 100 and the femoral mold 200 may each be made of a solid, unitary piece. The femoral mold 200 may be stretched over bones such that the femoral mold 200 may be adapted to fit over various sizes of bone, as will be discussed more fully below. It will be appreciated that both the tibial mold 100 and the femoral mold 200 may be manufactured using a variety of techniques currently known in the art, or which may become known in the future, for example, injection molding, compression molding or any other suitable technique may be used.

It will further be appreciated that the biocompatible material used to form either the tibial component 50 or femoral component 75 may be made from bone cement or other material that is presently known, or which may become known in the future, in the art to form such implants. Therefore, it should be noted that a myriad of other materials that are also biocompatibly suitable for surgical use may be utilized as the implant material without departing from the scope of the present invention.

Referring to FIGS. 1-3, the tibial mold 100, also referred to herein as a second mold, may comprise a main body portion 105, which may itself comprise a sidewall 102, an inner surface 110, an outer surface 120, an inner base surface 160, an outer base surface 160*a* and a cavity 130, sometimes referred to herein as a second cavity. The cavity 130 may be defined by the sidewall 102, sometimes referred to herein as a second sidewall, that extends around a perimeter 101 of the main body portion 105 of the tibial mold 100 and may be part of the inner surface 110. It will be appreciated that the structural features and elastic characteristics that permit the mold 100 to be located directly on the proximal surface of the tibia, may be referred to herein as a means for attaching the mold, in situ, directly to the patient's bone, and the means for attaching may comprise a circumferential elastic contacting means for circumferentially contacting a proximal portion of the tibia.

The inner base surface 160 of the tibial mold 100 may comprise at least one depression 170, and at least one protrusion, illustrated in FIG. 2 as two protrusions 172 and 174 (explained below in more detail) that may form an uneven surface in the inner base surface 160. The at least one depression 170 and the at least one protrusion 172 and 174 may be configured for forming a corresponding and opposing set of at least one protrusion and at least one depression in a tibial component 50 such that a natural tibial plateau may be simulated, at least in part. It will be appreciated that the uneven surface, if utilized, will only be uneven with respect to the inner base surface 160, and is not required to be uneven on the outer base surface 160*a*, although the outer base surface 160*a* could be uneven.

The cavity 130 may be characterized as having an open face 130*a* for receiving an amount of biocompatible material, such as bone cement, such that the biocompatible material may be configured for use as the tibial component 50. The tibial mold 100 with its open face 130*a*, may be further characterized by the absence of a substantially enclosed casing. As used herein, whether for the tibial mold 100 or the femoral mold 200, the phrase "substantially enclosed casing" may be defined as a mold that is substantially sealed along a majority of its outer surface such that an inner cavity is substantially surrounded on all sides, and the mold comprises at least one opening or port configured for venting the sealed mold, or for allowing the input of a biocompatible material therein, for example bone cement.

The outer surface 120 may define an outer, external shape of the tibial mold 100, and may be located opposite the inner surface 110. The outer, external shape of the tibial mold 100 may be shaped substantially as a kidney and corresponds to a cross sectional shape of the proximal portion of the natural tibial bone. It should be noted that the outer shape of the tibial mold 100 may be configured to correspond to the outer shape of a patient's tibial plateau, and any suitable outer shape for simulating the patient's tibial plateau may be used by the present invention.

A thickness "T" of the tibial mold 100 may be formed between the inner surface 110 and the outer surface 120. It should be noted that the thickness "T" may be altered to accommodate differing design features or characteristics requiring a thicker or thinner wall thickness. It is to be understood that any wall thickness of the tibial mold 100 of the present invention may be utilized and is contemplated by the present invention. By modifying the thickness "T" to be of any desired thickness, one of skill in the art may readily find a desirable thickness "T," without undue experimentation, to implement the requisite elasticity needed for a particular purpose for the tibial mold 100, as well as for the femoral mold 200.

The cavity 130 of the tibial mold 100 may be configured and dimensioned to receive the biocompatible material therein, for example bone cement. It will be appreciated that the tibial mold 100 may be placed, in situ, onto a patient's proximal tibial bone to form the resulting tibial component 50 directly thereon. The inner base surface 160 may have at least one depression 170 and at least one protrusion, illustrated in FIG. 2 as two protrusions 172 and 174, spaced in a particular arrangement such that the depression 170 and the protrusions 172 and 174 collectively result in a contour of the tibial component 50. It will be appreciated that the contour of the cavity 130 and the resulting tibial component 50 may simulate, at least in part, the surface of the natural tibial plateau. The resulting contour of the tibial component's 50 articulating surface is illustrated best in FIG. 1. It will be appreciated that the term "contour" as used herein may refer to the surface of the mold 100 that produces the articulating surface of the resulting tibial component 50, whether the articulating surface is flat, partially contoured with protrusions, or depressions, or a combination of both, or fully contoured with protrusions, or depressions, or a combination of both.

The depressions 52 and 54 of the tibial component 50 may be formed as a result of the cement being formed around the protrusions 172 and 174 of the tibial mold 100 (illustrated best in FIG. 2), respectively, which protrusions 172 and 174 may be located on the inner base surface 160. Further, depressions 52 and 54 may be configured and dimensioned to correspond with the prosthetic femoral condyles of the femoral component 75 in an articulating relationship, such that a new temporary joint may be formed, thus simulating, at least in part, the natural articular surface of the joint. It will be appreciated that by simulating at least a part of the natural articular surface of the joint, the patient may have at least a limited range of motion in the newly formed temporary prosthetic joint, during the time period between the removal of the old permanent prosthetic joint and the revisions surgery to implant a new permanent joint.

It will be appreciated that the prosthetic tibial plateau created by the tibial mold 100, and the prosthetic femoral condyles created by the femoral mold 200, while simulating the biomechanics of the natural joint to at least a limited extent, may not create a full range of motion in the joint. However, the prosthetic components that result from using the tibial mold 100 and the femoral mold 200 may be used to help the patient have at least some mobility and some limited range of motion in the joint. By so doing, the joint may not be immobilized completely, but may be able to bend and flex, thus avoiding soft tissue injury and increasing the patient's comfort during the 6-8 week time period when the prosthetic components are being utilized.

Further, the tibial mold 100 may comprise a depth reference feature, which depth reference feature may comprise a plurality of depth rings 150 and a plurality of markings 140. The depth rings 150 and the plurality of markings 140 may be formed on the outer surface 120 of the main body portion 105. It will be appreciated that a depth reference feature could also constitute the basic shape and size characteristics of the mold 100, which a skilled surgeon may utilize intuitively as a depth reference feature without the aid of depth rings 150, markings 140, and the like. It will be appreciated that the markings 140, if used, may correspond to different depth measurements used for increasing or decreasing the overall thickness of the tibial component 50 and bone cement needed to fit an extension gap between the tibial plateau and the femoral condyles. The markings 140 may be comprised of a series of numerals, or may be comprised of any other symbol used as a reference for representing a predetermined depth. It will be appreciated that a large extension gap between the tibia and the femur corresponds to a greater depth measurement needed to form the resulting tibial component 50, which is thick enough to properly fit the extension gap. It will be appreciated that the resulting tibial component 50 may ultimately provide an articulating surface in the knee joint.

In practice, the markings 140 may aid the surgeon in determining the proper thickness of the bone cement to be used for properly fitting between the extension gap, and for determining the proper spacing between the tibia and the femur. The markings 140 may be configured such that a surgeon may use the markings 140 of the tibial mold 100 as a guide for visually determining the thickness of bone cement to be used to fit the gap created between the tibia and femur in the knee joint. The thickness of the resulting tibial component 50 may be changed using a single tibial mold 100, according to the anatomical requirements of each individual patient.

The surgeon may determine the required thickness of the tibial component 50 using a variety of different methods, including: (1) forming the femoral component 75 first using the femoral mold 200, and then measuring the remaining gap using: (a) a spacer block, or (b) calipers, and then sizing the tibial mold 100 to correspond with the remaining gap; (2) gauging the size of the entire gap first, using (a) the spacer block, or (b) calipers, wherein the femoral component 75 comprises a predetermined thickness designed to occupy a predetermined space in the entire gap, and then subtracting the predetermined thickness of the femoral component 75 to arrive at a gap size for the tibial component; or (3) estimating the size of the gap by placing the tibial mold 100 near the gap to measure the distance between a proximal end of the tibia and a distal end of the femur using the markings 140 as a visual reference. It will be appreciated that the above may be referred to herein as a means for determining a gap size between the proximal tibia and distal femur. It will be appreciated that the spacer block or calipers may be used to gauge or measure the gap, indicating to the surgeon at which marking 140 to score, cut and/or trim the mold. Different spacer block sizes may correspond to each marking 140 indicated on the mold 100. After the proper thickness has been determined, the surgeon may use a scalpel or other instrument to score, cut, trim off and/or help peel off the excess portion of the tibial mold 100, specifically using depth rings 150 as a guide, creating a specific and properly sized mold 100 for that particular patient.

It will be appreciated that depth rings 150 may comprise a series of indentations, or grooves, for example V-grooves, or may even comprise protrusions in the outer surface 120 of the main body portion 105 for running an instrument, such as a scalpel or other surgical device along an edge, therein such that the series of indentations, or grooves may act as a guide to score, cut and/or trim the tibial mold 100. The depth rings 150 may correspond to the proper markings 140 and identify the proper thickness needed for the tibial component 50 to properly fit between the tibia and the femur. It will be appreciated that the surgeon may score, cut and/or trim the tibial mold 100 such that there is enough excess mold to securely wrap around the patient's proximal tibia while the biocompatible material, such as bone cement, cures on the bone.

After the thickness determination has been made, and the tibial mold 100 has been scored to the desired depth or desired thickness, biocompatible material, such as bone cement, may then be placed into the cavity 130 of the tibial mold 100. Prior to the biocompatible material completely curing, the tibial mold 100 may be located on the tibial bone where the biocompatible material may finish the curing process and harden. The tibial mold 100 may be located on a portion of the tibial bone by placing the tibial mold 100 into contact with a proximal surface of the tibia and/or surrounding tissue such that the biocompatible material may be positioned on the proximal surface of the tibia to thereby form the tibial component 50 directly on the proximal tibia.

It will be appreciated that the tibial mold 100 may be held in position by the surgeon or other surgical team member until the biocompatible material at least partially cures. It will further be appreciated that other mechanisms may be utilized by those of skill in the art to hold the tibial mold 100 in contact with the proximal surface of the tibia while allowing the biocompatible material to at least partially cure. The biocompatible material may cure directly on the proximal surface of the tibia, whether the curing process is partial or complete. When the tibial mold 100 is located on the tibial bone, a portion of the biocompatible material may enter into a cavity formed in the tibial bone, thus securing the resulting tibial component 50 to the tibial bone. Removal of the tibial mold 100 from the resulting tibial component 50 may be accomplished by scoring, cutting, tearing, ripping, splitting, peeling or otherwise manipulating the elastic tibial mold 100 from off of the tibial component 50 and tibial bone.

Referring briefly to both the tibial mold 100 and the femoral mold 200, it will be appreciated that elasticity is a feature of the present invention that may permit the femoral mold 200 to be advantageously stretched and wrapped around a bone during attachment and removal such that the mold 200 may be used in situ, such that a single mold may be used on a variety of differently sized bones. Elasticity may further permit the tibial mold 100 to be located, in situ, and may also permit the mold 100 to be scored or cut for peeling a portion of the mold away, or be trimmed away, thus permitting a single mold 100 to be used and adjusted to fit a number of different extension gap sizes and bone dimensions. The ability for the mold 100 or 200 to be readily peeled, scored, cut or trimmed due to its relatively low hardness may also be advantageous to separate the mold from the implant during removal.

The tibial mold 100, being elastic, can be constructed from a silicone or rubber material that possesses elastic memory, which causes the mold 100 to return to its original shape or position after being distorted. Therefore, the elastic memory of the material may provide enough strength for the mold 100 to substantially maintain its shape during the location of the prosthetic component 50 to the bone, and may also be flexible enough that one mold 100 may be used on several different bone sizes, while providing the ability to be peeled, cut, or torn away from the component 50 without adversely affecting the component 50.

It will be appreciated that a single mold may be used for attachment to bones of various sizes within a given range. It will further be appreciated that more than one size of mold 100 and 200 may be provided to accommodate all the potential possibilities in anatomical differences of patients. For example, three different mold sizes may be provided, such that each mold size has a different range of bone sizes on which the mold 100 or 200 will fit, i.e. small, medium, and large. It will be appreciated that more or less than three mold sizes may be used by the present invention, dependent upon the desired range of bones to be fitted by the molds.

Referring back to the tibial mold 100, the markings 140 may further delineate depth rings 150. The depth rings 150 may be formed either partially on or completely around the exterior of the tibial mold 100 such that the surgeon can immediately identify the requisite depth. Having identified a sufficient depth, the surgeon may shorten the tibial mold 100 using the depth rings 150 as a guide to score, cut and/or trim along the depth rings, due to the elastic nature of the mold, with a scalpel and peel away the excess portion of the tibial mold 100. Thus, because of the elastic capabilities of the material used to manufacture the tibial mold 100, a single mold 100 may be used to form many tibial components 50, of varying sizes in order to accommodate the differing anatomies of each patient, as well as the various extension gap sizes between the tibia and the femur.

Referring now to FIGS. 3-6, the femoral mold 200, also referred to herein as a first mold, may comprise an arcuate surface 205, a sidewall 202, an inner base surface 210 and an outer surface, generally referred to at 220. The inner base surface 210 and the sidewall 202 may define a cavity, sometimes referred to herein as a first cavity and generally referred to by item 230, which may be configured and dimensioned to receive an amount of biocompatible material, such as bone cement. It will be appreciated that the structural features provided herein, and the mold's 200 elastic characteristics, may be referred to herein as a means for attaching the mold, in situ, directly to the patient's bone, wherein the means for attaching may be a circumferential elastic gripping means for circumferentially gripping a proximal portion of the femur. As illustrated best in FIG. 5, the cavity 230 may be characterized as having an open face 230a for receiving the amount of biocompatible material, i.e. bone cement, which when cured will form the femoral component 75 (illustrated best in FIG. 6). The femoral mold 200, having an open face 230a, may further be characterized by the absence of a substantially enclosed casing. It will be appreciated that the outer surface 220 may define the outer shape of the femoral mold 200, which may be any suitable outer shape for simulating, at least in part, the natural biomechanics of the knee joint, and particularly the biomechanics of the patient's distal femur and femoral condyles.

A thickness "T" of the femoral mold 200 may be formed between the sidewall 202 and the outer surface 220. It should be noted that the thickness "T" may be altered to accommodate different design features or characteristics requiring a thicker or thinner wall thickness. It is to be understood that any wall thickness of the femoral mold 200 of the present invention may be utilized by modifying the thickness "T" to be of any desired thickness to provide the desired amount of elasticity to the mold 200.

The femoral mold 200 may have a main body portion 226 and two leg portions, a first leg portion 222 and a second leg portion 224, extending generally from the main body portion 226 in a substantially arcuate manner, as illustrated. It will be appreciated that the first leg portion 222 may be a medial leg 222, and the second leg portion 224 may be a lateral leg 224. The medial leg 222 and the lateral leg 224 may each have an inner surface, designated as items 222a and 224a, and an outer surface, designated as items 222b and 224b, to form the resulting femoral condyles 82 and 84. The arcuate shape of the inner surface of the femoral mold 200 may result in rounded artificial femoral condyles 82 and 84, which may be configured to articulate with the tibial component's 50 depressions 52 and 54 such that the natural biomechanics of the femoral condyles may be simulated, at least in part. A gap, generally referred to at 228, may separate the medial leg 222 from the lateral leg 224. The gap 228 may be defined by a junction between the two leg portions 222 and 224 forming a crotch 238, and allows the resulting femoral component 75 and its two condyles 82 and 84 to straddle a raised portion 56 formed on the tibial component 50, while articulating with tibial depressions 52 and 54.

The articulation between the two artificial condyles 82 and 84 of the femoral component 75 and the corresponding surface of the tibial component 50 is a feature that allows patients to bend their knees at the joints, resulting in at least a limited range of motion. Thus, the tibial mold 100 and the femoral mold 200 may each have the capability to form implants that simulate, at least in part, the natural articulation surfaces of the knee joint, so that patients may enjoy a limited range of motion in the knee joint, which advantageously provides the basis for a successful subsequent surgery.

The main body portion 226 may further comprise a first engagement side, generally referred to in FIG. 5 at 212, and a second engagement side, generally referred to in FIG. 5 at 214, each of which engages a different portion of the distal femur. A separation distance, referred to as item 216 in FIG. 4, may be formed between the first engagement side 212 and the second engagement side 214, and may be dimensioned to be less than a width of the distal end of the femur, such that some elasticity in the femoral mold 200 may be required in order for the mold 200 to stretch around or over a portion of the femur.

The cavity 230 of the femoral mold 200 may be further defined by the sidewall 202, sometimes referred to herein as a first sidewall, that may extend around a perimeter 201 of the main body portion 226 of the femoral mold 200. The sidewall 202 may comprise an edge 232, and surrounds the cavity 230 such that the sidewall 202 aids in maintaining the fixation material within the cavity 230 of the mold 200. Specifically, the sidewall 202 may function as a barrier and may provide an upper surface or wall, where the bone cement or other suitable biocompatible material may be poured into the cavity 230 and retained within the cavity 230 by said sidewall 202.

It will be appreciated that an angular portion 234 may extend from the sidewall 202 to the outer surface 220 to connect the sidewall 202 and the outer surface. It should be noted that angular portion 234 may be rounded and may be configured for connecting the sidewall 202 to the outer surface 220 and may include any size and shape in order to connect the sidewall 202 to the outer surface 220.

The inner base surface 210 may have an inner contour that produces the femoral component 75 that has a resulting exterior contour simulating, at least in part, the shape and function of the natural femoral condyles. It will be appreciated that the term "contour" as used herein may refer to the surface of the mold 200 that produces the articulating surface of the resulting component 75, whether the articulating surface comprises a flat contour, a rounded contour, or is partially contoured with protrusions, or depressions, or a combination of both, or fully contoured with protrusions, or depressions, or a combination of both. Specifically, the lateral leg 222 and the medial leg 224 form the main articulating surfaces of the resulting femoral component 75 and simulate, at least in part, the natural femoral condyles. A protruding arched surface 236 may protrude from the inner base surface 210, which may form a corresponding mild depression 80 in the resulting femoral component 75, which depression 80 may be one portion of the femoral component 75 that articulates with a portion of the tibial component 50.

An eyelet 270 may extend in an upward direction from the top of the femoral mold 200 for aiding the surgeon in wrapping the femoral mold 200 around the distal femur and for further aiding in the separation of the femoral mold 200 from the femoral component 75. The eyelet 270 may be shaped in as a loop with a rounded top 270a and two ends 270b and 270c connected to the main body portion 226, as illustrated in FIGS. 4-6, or the eyelet 270 may have a square shape, an elongated shape, a triangular shape, a polygonal shape, or any other suitable shape for aiding the surgeon in locating the femoral mold 200 on the bone, and removing said femoral mold 200 from the bone.

The femoral mold 200 may be configured and dimensioned such that it may be wrapped around the distal femur or bone surface, even after the mold 200 has been substantially filled with biocompatible material. Wrapping the femoral mold 200 may result in the biocompatible material, which is maintained within the cavity 230 of the femoral mold 200 by the sidewall 202, mating with the distal femur to thereby adhere the biocompatible material to the bone, forming the femoral component 75. By so doing, the mold 200 may stretch around the distal femur, and the outer surface geometry of the distal femur may be closely matched due to the stretching of the elastic mold 200 resulting in a properly sized femoral component 75 being formed on the bone, while simultaneously securely fastening the femoral component 75 to the bone preventing any unwanted movement.

The femoral mold 200 also has the ability to be peeled or torn off once the bone cement has cured, due at least in part to the elasticity of the material from which the femoral mold 200 may be comprised. Additionally, the elasticity of the femoral mold 200 permits the mold to accommodate and be attached to a variety of distal femur sizes. The elasticity of the material may be a feature in both the tibial mold 100 and the femoral mold 200.

Removal of the femoral mold 200 from the resulting femoral component 75 may be accomplished by pulling the mold 200 off of the femoral component 75 and femoral bone, or by scoring, cutting, tearing, ripping, splitting, trimming, peeling and otherwise pulling and manipulating the elastic femoral mold 200 from the bone. Elasticity of the femoral mold 200 advantageously provides the capability for the mold 200 to stretch and wrap around a bone during attachment. The elastic capability, therefore, allows a single femoral mold 200 to accommodate and attach to many different sizes of distal femurs. Elasticity also provides the capability for the femoral mold 200 to be easily separated from the femoral component 75 and bone during removal.

The femoral mold 200, being elastic, may be constructed from a silicone or rubber material, and possesses elastic memory, which causes the mold 200 to return to its original shape or position after distortion. Therefore, the elastic memory of the material may provide enough strength for the mold 200 to maintain its shape during the attachment of the femoral mold 200 to the femoral bone, and may also be flexible enough that one mold 200 may be used for several different sizes of bone, while providing the ability to easily be pulled from off of the femoral component 75, or cut or torn from the femoral component 75 without adversely affecting the component 75.

In practice, the femoral mold 200 may be used in situ by the surgeon in the following manner. First, bone cement, or another biocompatible material known in the art for temporary fabrication of femoral components 75, may be mixed and poured into the cavity 230 of the femoral mold 200. The surgeon may then scrape the edge 232 of the sidewall 202 with a knife or other appropriate instrument to appropriately pack and level the cement within the femoral mold 200.

Second, the bone cement located within the cavity 230 of the femoral mold 200 may be allowed to cure slightly, after which the femoral mold 200 may be located on the distal end of the femur, where the bone cement may be allowed to completely cure. During the location process, the femoral mold 200 may be stretched and pressed firmly around the distal portion of the bone so that a tight connection between the bone and the mold 200 may be formed. Additionally, the bone cement may contact the surface of the bone causing the bone cement to adhere to the bone.

The elasticity of the material comprising the femoral mold 200 permits the mold 200 to wrap around and attach to the distal femur by forcing the first engagement side 212 away from the second engagement side 214 such that the separation distance 216 may be enlarged momentarily thereby allowing the mold 200 to be attached to the distal femur. At this point, the elastic memory of the mold 200 causes the first engagement side 212 and the second engagement side 214 to return substantially back to their original shape. The mold 200 may be, therefore, pressed onto the distal femur such that a secure, friction fit between the mold 200 and the bone may be obtained. It will be appreciated that the term friction fit includes a press fit, a compression fit, an interference fit and the like.

Once the cement has completely cured and hardened, the surgeon may remove the elastic femoral mold 200 by any one of a variety of methods, including pulling the mold 200 from off of the femoral component 75, or cutting a portion of the mold 200 and tearing the remainder of the mold 200 away from the resulting femoral component 75, or simply using the eyelet 270 to pull or tear the mold 200 from the component 75. Other examples of the methods of removal include: scoring, cutting, tearing, ripping, splitting, peeling and otherwise pulling the mold 200 apart from said bone. The removal process acts as the last step in forming the femoral component 75 on the bone. It will be appreciated that the removal of the femoral mold 200 may be accomplished by a variety of methods utilizing a variety of devices, each of which are intended to fall within the scope of the present invention.

It will be appreciated that the structure and apparatus disclosed herein is merely one example of a means for attaching the mold, in situ, directly to the bone, and it should be appreciated that any structure, apparatus or system for attaching the mold to the bone which performs functions the same as, or equivalent to, those disclosed herein are intended to fall within the scope of a means for attaching the mold to the bone, including those structures, apparatus or systems for attaching the mold to the bone which are presently known, or which may become available in the future. Anything which functions the same as, or equivalently to, a means for attaching the mold to the bone falls within the scope of this element.

In accordance with the features and combinations described above, a useful method of implanting a tibial mold 100 on a patient's knee joint includes the steps of:
 (a) providing an elastic tibial mold, said tibial mold having a sidewall defining a cavity;
 (b) determining a desired thickness of a tibial component of a knee replacement to fit a portion of an extension gap by measuring the distance between the distal end of the femur and the proximal end of the tibia by utilizing a marking formed on an outer surface of the tibial mold;
 (c) scoring the tibial mold at the level of the desired thickness marking and utilizing a depth ring as a guide for a cutting device, wherein said depth ring may at least partially circumscribe the tibial mold;
 (d) removing the excess portion of the tibial mold such that only the desired thickness of the resulting tibial component may be formed;
 (e) providing a biocompatible material, configured for use as the tibial component, and substantially filling the cavity of the tibial mold with said biocompatible material to the previously determined thickness;
 (f) positioning the tibial mold on the proximal end of the tibia;
 (g) permitting the biocompatible material to at least partially cure; and
 (h) removing the tibial mold from the bone and the resulting tibial component.

In accordance with the features and combinations described above, a useful method of implanting a femoral mold 200 on a patient's knee joint includes the steps of:
 (a) providing an elastic femoral mold, said femoral mold having a sidewall defining a cavity;
 (b) providing a biocompatible material, configured for use as a femoral component, and substantially filling the cavity of the femoral mold with said biocompatible material to a desired thickness;
 (c) positioning the femoral mold on the distal end of the femur by stretching and firmly wrapping the femoral mold around a distal portion of the femur;
 (d) permitting the biocompatible material to at least partially cure; and
 (e) removing the femoral mold from the bone and the resulting femoral component, including pulling, scoring, cutting, tearing and peeling the femoral mold away from said bone and said femoral component.

Those having ordinary skill in the relevant art will appreciate the advantages provided by the features of the present invention. For example, it is a potential feature of the present invention to provide a disposable knee mold system which is simple in design and manufacture. Another potential feature of the present invention is to provide such a disposable knee mold system that is elastic, and relatively inexpensive to manufacture such that the molds may be used once and then disposed of, and modified to fit the anatomy of a particular patient. It is a further potential feature of the present invention, in accordance with one aspect thereof, to provide a knee mold system that is manufactured from an elastic material possessing elastic memory such that the mold may be stretched and deformed in order to secure the mold to the bone of the knee joint, without maintaining such a deformed shape. It is a further potential feature of the present invention to provide a knee mold system that permits the molds to be located on the bone, in situ, during surgery. It is yet another potential feature of the present invention to provide a knee mold system that comprises a femoral mold and a tibial mold, both of which may be formed as a unitary piece. It is another potential feature of the present invention to provide a knee mold system that may accommodate varying anatomical differences within a given range using a single tibial mold and a single femoral mold. It is still another potential feature of the present invention to provide a knee mold system that may be located on the bone permitting the formation of an implant and then subsequently removed easily from the bone and implant by way of pulling, peeling, cutting, scoring and tearing the mold without adversely affecting the implant. It is another potential feature of the present invention to provide a knee mold system that forms a resulting tibial implant and femoral implant that simulate the biomechanics of the natural knee joint, at least in part, such that a patient may have some mobility and some range of motion in the knee joint during the time period the temporary prosthetic implant is located within the knee joint and before the revision surgery.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method of forming at least one component of a temporary prosthetic knee joint on a bone during an in situ surgical procedure, the method comprising the steps of:
 providing an elastic mold configured and dimensioned for being affixed to a portion of the bone, said elastic mold having a cavity defined by a sidewall, wherein the elastic mold comprises an elastic femoral mold that is characterized by the absence of a substantially enclosed casing;

placing an amount of biocompatible material within the cavity of the elastic mold for forming the at least one component of the prosthetic knee joint;

positioning the elastic mold on the portion of the bone; and removing the elastic mold from said portion of said bone after the amount of biocompatible material has been at least partially cured thereby forming said at least one component.

2. The method of forming at least one component of a temporary prosthetic knee joint of claim 1, wherein the step of providing an elastic mold further comprises providing an elastic femoral mold having a protruding arched surface on an interior surface that forms a depression in a resulting femoral prosthesis.

3. The method of forming at least one component of a temporary prosthetic knee joint of claim 1, wherein the step of providing an elastic mold further comprises providing an elastic femoral mold, wherein said cavity is characterized by an open face.

4. The method of forming at least one component of a temporary prosthetic knee joint of claim 1, wherein the step of providing an elastic mold further comprises providing an elastic femoral mold, wherein the femoral mold has an eyelet for aiding a surgeon in wrapping the femoral mold around a distal portion of a femur and for further aiding in the removal of said femoral mold by separating the femoral mold from a resulting femoral prosthesis.

5. The method of forming at least one component of a temporary prosthetic knee joint of claim 1, wherein the step of providing an elastic mold further comprises providing an elastic femoral mold, wherein the sidewall extends around a perimeter of the femoral mold, and said sidewall is configured to provide a barrier such that the biocompatible material is substantially retained within said cavity by said sidewall.

6. The method of forming at least one component of a temporary prosthetic knee joint of claim 1, wherein the step of providing an elastic mold further comprises providing an elastic femoral mold, wherein the femoral mold has a main body portion, a medial leg and a lateral leg, each leg having a substantially arcuate inner surface designed to form a prosthetic femoral condyle to simulate, at least in part, the biomechanics of the natural femoral condyle such that the prosthetic femoral condyle is configured to articulate with a tibial surface.

7. The method of forming at least one component of a temporary prosthetic knee joint of claim 6, wherein the step of providing the elastic mold comprises providing the femoral mold with a gap formed between the medial leg and the lateral leg, wherein the medial leg joins the lateral leg at a junction, said junction defining a crotch portion of the main body portion.

8. The method of forming at least one component of a temporary prosthetic knee joint of claim 1, wherein the step of providing an elastic mold further comprises providing an elastic femoral mold, wherein the femoral mold comprises an elastic material such that the femoral mold is configured to be wrapped around a distal portion of a patient's femur to bring the biocompatible material into contact with a surface of the distal portion of the femur, wherein said elastic material permits the femoral mold to stretch, thereby allowing a single femoral mold to accommodate various distal femur sizes, and also aids a surgeon in removing the femoral mold from the femur.

9. The method of forming at least one component of a temporary prosthetic knee joint of claim 1, wherein the step of providing an elastic mold further comprises manufacturing said elastic mold from an elastic material, and said elastic mold is designed for being used once and then disposed of, and wherein the elastic mold is configured to allow a surgeon to alter and adjust the mold to accommodate an anatomy of a patient.

10. The method of forming at least one component of a temporary prosthetic knee joint of claim 1, wherein the step of placing the amount of biocompatible material within the cavity further comprises substantially filling the femoral mold with said biocompatible material to a desired thickness.

11. The method of forming at least one component of a temporary prosthetic knee joint of claim 1, wherein the step of positioning the elastic mold on the portion of the bone further comprises locating the femoral mold on a distal end of a femur by stretching and firmly wrapping the femoral mold around a distal portion of the femur.

12. The method of forming at least one component of a temporary prosthetic knee joint of claim 1, wherein the step of placing the amount of biocompatible material within the cavity further comprises the step of permitting the biocompatible material to slightly cure before positioning the elastic mold on the portion of the bone.

13. The method of forming at least one component of a temporary prosthetic knee joint of claim 1, wherein the step of removing the elastic mold further comprises scoring, cutting, tearing, ripping, splitting, peeling and otherwise pulling the femoral mold away from the bone and a resulting femoral component of the prosthetic knee joint.

14. The method of forming at least one component of a temporary prosthetic knee joint of claim 1, wherein the step of providing an elastic mold further comprises providing a tibial mold, wherein the tibial mold has an inner base surface comprising at least one protrusion and at least one depression, which are configured for forming a corresponding and opposing at least one depression and at least one protrusion in a tibial component of the prosthetic knee joint so as to simulate, at least in part, a natural tibial plateau.

15. The method of forming at least one component of a temporary prosthetic knee joint of claim 1, wherein the step of providing an elastic mold further comprises providing a tibial mold, wherein the tibial mold has a plurality of markings formed on an outer surface of the tibial mold so as to provide a guide for visually determining a thickness of bone cement needed for fitting between an extension gap formed between a patient's tibial bone and femoral bone.

16. The method of forming at least one component of a temporary prosthetic knee joint of claim 15, wherein the plurality of markings further comprises a series of symbols representing a predetermined size and thickness of a femoral prosthesis.

17. The method of forming at least one component of a temporary prosthetic knee joint of claim 1, wherein the step of providing an elastic mold further comprises providing a tibial mold, wherein the tibial mold has a plurality of depth rings for scoring, cutting and peeling off an excess portion of said tibial mold, said plurality of depth rings comprising a series of indentations in an outer surface of the tibial mold configured for running a cutting instrument in said plurality of depth rings such that the series of indentations acts as a guide.

18. The method of forming at least one component of a temporary prosthetic knee joint of claim 1, wherein the step of providing an elastic mold further comprises providing a tibial mold, wherein the tibial mold has an external shape defined by an outer surface of said tibial mold, wherein said external shape is substantially kidney shaped and corresponds to a cross sectional shape of a natural tibial bone.

19. The method of forming at least one component of a temporary prosthetic knee joint of claim 1, wherein the step of providing an elastic mold further comprises providing an elastic tibial mold that is characterized by the absence of a substantially enclosed casing.

20. The method of forming at least one component of a temporary prosthetic knee joint of claim 1, wherein the method further comprises the step of making a depth determination that corresponds to a size of a resulting tibial component of the prosthetic knee joint by measuring an extension gap between a distal end of a femur and a proximal end of a tibia by utilizing a marking formed on an outer surface of a tibial mold.

21. The method of forming at least one component of a temporary prosthetic knee joint of claim 20, wherein the method further comprises the step of scoring the tibial mold at a desired thickness at the marking by utilizing a plurality of depth rings configured for use as a guide, wherein said plurality of depth rings at least partially circumscribe the tibial mold.

22. The method of forming at least one component of a temporary prosthetic knee joint of claim 21, wherein the method further comprises the step of removing an excess portion of the tibial mold such that only the desired thickness for forming the resulting tibial component of the prosthetic knee joint remains.

23. The method of forming at least one component of a temporary prosthetic knee joint of claim 1, wherein the step of placing the amount of biocompatible material within the cavity further comprises substantially filling the cavity of a tibial mold with said biocompatible material to a previously determined depth.

24. The method of forming at least one component of a temporary prosthetic knee joint of claim 1, wherein the step of positioning the elastic mold on the bone further comprises positioning a tibial mold on a proximal end of a tibia.

25. The method of forming at least one component of a temporary prosthetic knee joint of claim 1, wherein the step of placing the amount of biocompatible material within the cavity further comprises placing said biocompatible material in a tibial mold and permitting the biocompatible material to slightly cure before positioning the tibial mold on the bone.

26. The method of forming at least one component of a temporary prosthetic knee joint of claim 1, wherein the step of removing the elastic mold further comprises removing a tibial mold from the bone and a resulting tibial component of the prosthetic knee joint.

27. The method of forming at least one component of a temporary prosthetic knee joint of claim 1, wherein the step of positioning the elastic mold on the portion of the bone further includes stretching the elastic mold around said portion of said bone to thereby affix the elastic mold to said bone in a friction fit.

28. The method of forming at least one component of a temporary prosthetic knee joint of claim 1, wherein the method further comprises ascertaining a gap size using a means for determining the gap size between a proximal region of a tibia and a distal region of a femur for receipt of the prosthetic component and providing an articulation surface that allows for at least some range of motion with a complementary prosthetic component.

29. The method of forming at least one component of a temporary prosthetic knee joint of claim 28, wherein the means for determining a gap size includes a spacer block.

30. The method of forming at least one component of a temporary prosthetic knee joint of claim 28, wherein the means for determining a gap size includes calipers.

31. A method of forming at least one component of a temporary prosthetic knee joint on a bone during an in situ surgical procedure, the method comprising the steps of:
provviding an elastic mold configured and dimensioned for being affixed to a portion of the bone, said elastic mold having a cavity defined by a sidewall, wherein the elastic mold comprises an elastic femoral mold, wherein the femoral mold has a main body portion, a medial leg and a lateral leg, each leg having a substantially arcuate inner surface designed to form a prosthetic femoral condyle to simulate, at least in part, the biomechanics of the natural femoral condyle such that the prosthetic femoral condyle is configured to articulate with a tibial surface;
placing an amount of biocompatible material within the cavity of the elastic mold for forming the at least one component of the prosthetic knee joint;
positioning the elastic mold on the portion of the bone; and
removing the elastic mold from said portion of said bone after the amount of biocompatible material has been at least partially cured thereby forming said at least one component.

32. A method of forming at least one component of a temporary prosthetic knee joint on a bone during an in situ surgical procedure, the method comprising the steps of:
providing an elastic mold configured and dimensioned for being affixed to a portion of the bone, said elastic mold having a cavity defined by a sidewall, wherein the elastic mold comprises a tibial mold, wherein the tibial mold has an inner base surface comprising at least one protrusion and at least one depression, which are configured for forming a corresponding and opposing at least one depression and at least one protrusion in a tibial component of the prosthetic knee joint so as to simulate, at least in part, a natural tibial plateau;
placing an amount of biocompatible material within the cavity of the elastic mold for forming the at least one component of the prosthetic knee joint;
positioning the elastic mold on the portion of the bone; and
removing the elastic mold from said portion of said bone after the amount of biocompatible material has been at least partially cured thereby forming said at least one component.

33. A method of forming at least one component of a temporary prosthetic knee joint on a bone during an in situ surgical procedure, the method comprising the steps of:
providing an elastic mold configured and dimensioned for being affixed to a portion of the bone, said elastic mold having a cavity defined by a sidewall, wherein the elastic mold comprises a tibial mold, wherein the tibial mold has an external shape defined by an outer surface of said tibial mold, wherein said external shape is substantially kidney shaped and corresponds to a cross sectional shape of a natural tibial bone;
placing an amount of biocompatible material within the cavity of the elastic mold for forming the at least one component of the prosthetic knee joint;
positioning the elastic mold on the portion of the bone; and
removing the elastic mold from said portion of said bone after the amount of biocompatible material has been at least partially cured thereby forming said at least one component.

34. A method of forming at least one component of a temporary prosthetic knee joint on a bone during an in situ surgical procedure, the method comprising the steps of:
providing an elastic mold configured and dimensioned for being affixed to a portion of the bone, said elastic mold having a cavity defined by a sidewall, wherein the elastic mold comprises an elastic tibial mold that is characterized by the absence of a substantially enclosed casing;

placing an amount of biocompatible material within the cavity of the elastic mold for forming the at least one component of the prosthetic knee joint;

positioning the elastic mold on the portion of the bone; and removing the elastic mold from said portion of said bone after the amount of biocompatible material has been at least partially cured thereby forming said at least one component.

35. A method of forming at least one component of a temporary prosthetic knee joint on a bone during an in situ surgical procedure, the method comprising the steps of:

providing an elastic mold configured and dimensioned for being affixed to a portion of the bone, said elastic mold having a cavity defined by a sidewall, wherein the elastic mold comprises an elastic tibial mold that is characterized by the absence of a substantially enclosed casing;

ascertaining a gap size using a means for determining the gap size between a proximal region of a tibia and a distal region of a femur for receipt of the prosthetic component;

placing an amount of biocompatible material within the cavity of the elastic mold for forming the at least one component of the prosthetic knee joint;

positioning the elastic mold on the portion of the bone;

removing the elastic mold from said portion of said bone after the amount of biocompatible material has been at least partially cured thereby forming said at least one component; and providing an articulation surface that allows for at least some range of motion with a complementary prosthetic component.

* * * * *